United States Patent
Perez Grossmann

(10) Patent No.: US 9,795,503 B2
(45) Date of Patent: Oct. 24, 2017

(54) METHOD AND APPARATUS FOR TRABECULECTOMY AND SUPRACHOROIDAL SHUNT SURGERY

(71) Applicant: Rodolfo Alfredo Perez Grossmann, Lima (PE)

(72) Inventor: Rodolfo Alfredo Perez Grossmann, Lima (PE)

( * ) Notice: Subject to any disclaimer, the term of this patent is extended or adjusted under 35 U.S.C. 154(b) by 376 days.

(21) Appl. No.: 14/057,653

(22) Filed: Oct. 18, 2013

(65) Prior Publication Data
US 2015/0112372 A1    Apr. 23, 2015

(51) Int. Cl.
| | | |
|---|---|---|
| *A61F 9/00* | (2006.01) | |
| *A61B 17/34* | (2006.01) | |
| *A61B 17/3205* | (2006.01) | |
| *A61F 9/007* | (2006.01) | |

(52) U.S. Cl.
CPC ............ *A61F 9/00* (2013.01); *A61B 17/3205* (2013.01); *A61B 17/34* (2013.01); *A61F 9/00781* (2013.01)

(58) Field of Classification Search
CPC . A61B 10/02; A61B 10/0233; A61B 10/0266; A61B 10/0275; A61B 17/0467; A61B 17/3205; A61B 17/32053; A61B 17/32075; A61B 17/34; A61B 17/3401; A61F 9/00781; A61F 9/00709; A61F 9/00736; A61F 9/00745; A61F 9/00763; A61F 9/00754

See application file for complete search history.

(56) References Cited

U.S. PATENT DOCUMENTS

| | | |
|---|---|---|
| 4,874,375 A | 10/1989 | Ellison |
| 5,342,370 A | 8/1994 | Simon et al. |
| 5,676,679 A | 10/1997 | Simon et al. |
| 5,718,237 A | 2/1998 | Haaga |
| 6,666,841 B2 | 12/2003 | Gharib et al. |
| 6,709,408 B2 | 3/2004 | Fisher |
| 6,726,664 B2 | 4/2004 | Yaron et al. |
| 6,872,185 B2 | 3/2005 | Fisher |
| 6,890,309 B2 | 5/2005 | Fisher |
| 7,670,310 B2 | 3/2010 | Yaron et al. |
| D657,461 S | 4/2012 | Schembre et al. |
| 8,313,454 B2 | 11/2012 | Yaron et al. |
| 2006/0052722 A1 | 3/2006 | Brautigam et al. |
| 2009/0287233 A1 | 11/2009 | Huculak |
| 2010/0114006 A1 | 5/2010 | Baerveldt |
| 2012/0253228 A1 | 10/2012 | Schembre et al. |

OTHER PUBLICATIONS

Merriam-Webster definition of "solid" as accessed Aug. 3, 2016; http://www.merriam-webster.com/dictionary/solid.*
H.A. Quigley et al., "The number of people with glaucoma worldwide in 2010 and 2020", *British Journal of Ophthalmology*, 2006 (month unknown), pp. 262-267, vol. 90, No. 3.
J.E. Cairns, "Trabeculectomy: Preliminary Report of a New Method", *American Journal of Ophthalmology*, Oct. 1968, pp. 673-679, vol. 66, No. 4.

(Continued)

*Primary Examiner* — Jonathan Miles
(74) *Attorney, Agent, or Firm* — Buchanan, Ingersoll & Rooney PC

(57) ABSTRACT

A medical device and surgical procedure for the treatment of glaucoma in patients with primary open angle glaucoma, secondary open angle glaucoma, closed angle glaucoma, and refractory glaucoma. The device is inserted between two scleral flaps, cutting the trabecular meshwork and the sclera. When the device is removed, a proximal-facing cutting edge forms a tunnel allowing the aqueous humor to flow out of the anterior chamber into the suprachoroidal space.

7 Claims, 4 Drawing Sheets

(56) References Cited

OTHER PUBLICATIONS

J.T. Wilensky et al., "The Effects of Glaucoma Filtering Surgery on the Variability of Diurnal Intraocular Pressure", *Transactions of the American Ophthalmological Society*, 1994, pp. 377-383, vol. 92.

P.R. Lichter et al., "Interim Clinical Outcomes in the Collaborative Initial Glaucoma Treatment Study Comparing Initial Treatment Randomized to Medications or Surgery", *Ophthalmology*, 2001, pp. 1943-1953, vol. 108, No. 11, Elsevier Science Inc.

A.C. Molteno et al., "Long-term Results of Primary Trabeculectomies and Molteno Implants for Primary Open-Angle Glaucoma", *Arch. Ophthalmology*, Sep. 1, 2011, pp. 1742-1750, vol. 106, No. 9.

A. Bill, "The aqueous humor drainage mechanism in the cynomolgus monkey (*Macaca irus*) with evidence for unconventional routes", *Investigative Ophthalmology*, Oct. 1965, pp. 911-919, vol. 4, No. 5.

J.F. Jordan et al., "A Novel Approach to Suprachoroidal Drainage for the Surgical Treatment of Intractable Glaucoma", *Journal of Glaucoma*, Jun. 2006, pp. 200-205, vol. 15, No. 3, Lippincott Williams & Wilkins.

K. Ito et al., "Supraciliochoroidal Fluid in the Eyes Indicates Good Intraocular Pressure Control Despite Absence of Obvious Filtering Bleb after Trabeculectomy", *Journal of Glaucoma*, 2002, pp. 540-542, vol. 11, No. 6, Lippincott Williams & Wilkins, Inc.

International Search Report and Written Opinion mailed in the corresponding PCT application on Jun. 11, 2015 (12 pages).

\* cited by examiner

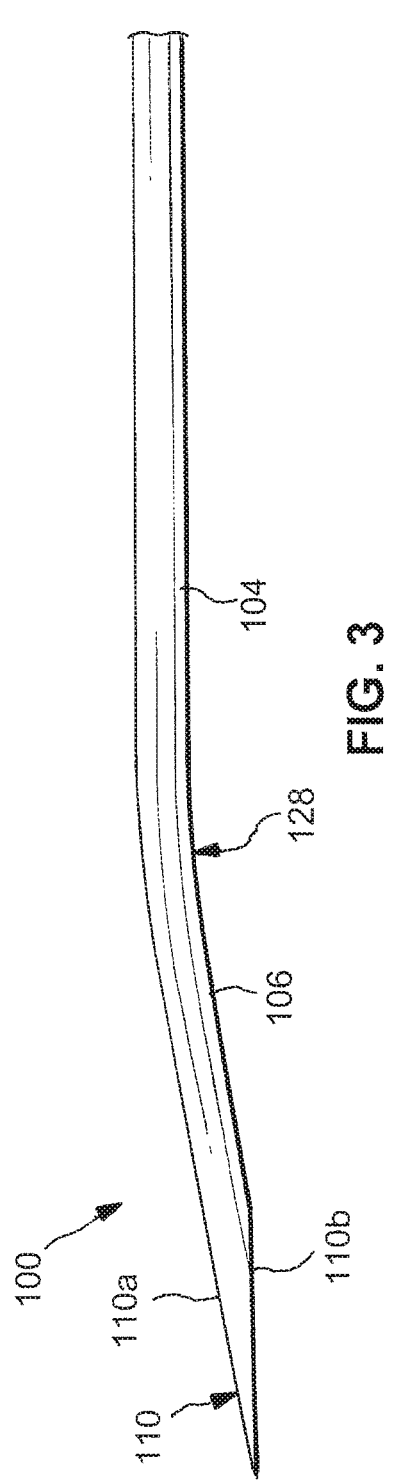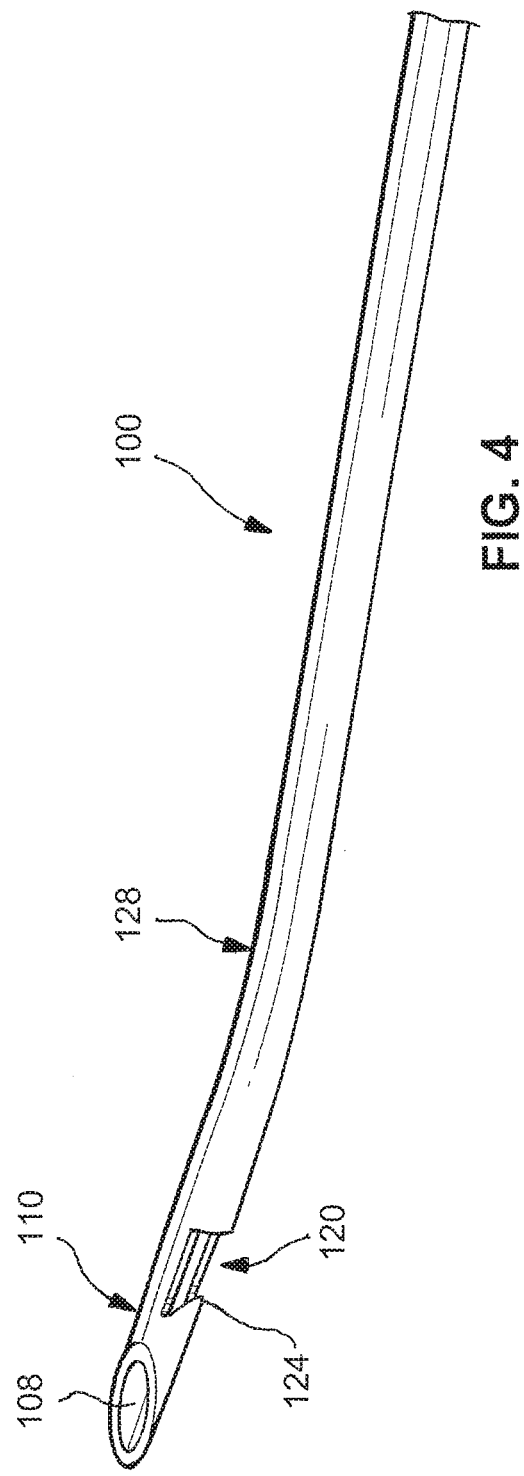

METHOD AND APPARATUS FOR TRABECULECTOMY AND SUPRACHOROIDAL SHUNT SURGERY

FIELD OF THE INVENTION

This invention relates to a novel medical device and surgical procedure for the treatment of glaucoma in patients with primary and secondary open angle glaucoma, closed-angle glaucoma, and refractory glaucoma.

BACKGROUND

The present invention generally relates to medical devices and methods for reducing intraocular pressure in the eye of mammals. More particularly, the present invention relates to the treatment of glaucoma via the use of a bent surgical device to surgically create a channel thereby permitting aqueous humor to flow out of the anterior chamber into the suprachoroidal space.

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

Glaucoma is the second leading cause of blindness worldwide (Quigley H A and A T Broman, BR J OPHTHALMOL 90(3): 262-267 (2006)). Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is a major treatment goal in glaucoma.

In glaucomas associated with an elevation in eye pressure (intraocular hypertension), the source of resistance to outflow is mainly in the trabecular meshwork. The tissue of the trabecular meshwork allows the aqueous humor to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous humor and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, pseudo-exfoliation glaucoma, or diseases such as hyperthyroidism that produce vascular congestion. Glaucoma may also be referred to as "refractory" or "complicated," both of which describe glaucoma that does not respond to typical drugs and treatments.

All current therapies for glaucoma are directed at decreasing intraocular pressure. Medical therapy includes topical ophthalmic drops or oral medications that reduce the production or increase the outflow of aqueous humor. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. U.S. Pat. No. 6,666,841 to Gharib et al. describes a trabecular shunt and a method for treating glaucoma comprising placing a trabecular shunt thorough diseased trabecular meshwork. U.S. Pat. No. 6,726,664 to Yaron et al. describes an implant having a tube for permitting fluid flow and delivery device for implanting the implant. U.S. Pat. No. 7,670,310 to Yaron et al. describes an implant and delivery device for implanting the implant in the eye. U.S. Pat. No. 5,342,370 to Simon et al. and related U.S. Pat. No. 5,676,679 to Simon et al. relate to a method and device used to insert an artificial meshwork in order to treat an eye with glaucoma and lower the intraocular pressure of the eye.

Needles and tissue cutting devices are known in the art and include U.S. Patent Application Publication No. 2012/0253228 to Schembre et al. and related U.S. Design Pat. No. D657461 to Schembre et al. which relate to a. biopsy needle tip and endoscopic ultrasound-guided biopsy needle. U.S. Pat. No. 4,874,375 to Ellison et al, relates to an improved tissue retractor particularly adapted for use during arthroscopic surgery. U.S. Pat. No. 5,718,237 to J R Haaga relates to a side cut needle including a solid stylet telescopically received within an inner tubular cannula which is telescopically received within an outer tubular cannula. U.S. Pat. Nos. 6,709,408, 6,872,185, and 6,890,309 to John Fisher describe a dual action biopsy needle that scrapes tissue of cellular thickness from a lesion during forward and rearward reciprocations of the needle along its longitudinal axis of symmetry. U.S. Patent Application Publication No. 2006/0052722 to Brautigam et al. describes a specimen retrieving needle having a closed lead end and with an outside diameter of less than 1.0 mm U.S. Patent Application Publication No. 2009/0287233 to J Huculak describes a small gauge mechanical tissue cutter/aspirator probe useful for removing the trabecular meshwork of a human eye.

Trabeculectomy has been the glaucoma surgery of choice since it was described for the first time in 1968 (Cairns J E, AM J OPHTHALMOL 66(4): 673-9 (1968)). Trabeculectomy is often augmented with topically applied anticancer drugs, such as 5-flurouracil or mitomycin-C to decrease scarring and increase the likelihood of surgical success.

Several studies have shown that trabeculectomy provides lower intraocular pressure (IOP) and reduces TOP daily fluctuation when compared with medical therapy (Wilensky J T et al., TRANS AM OPHTHALMOL SOC 92: 377-81 (1994); Lichter P R, et al., OPHTHALMOLOGY 108(11): 1943-53 (2001)). However, at least 20% of eyes with trabeculectomy will require glaucoma medication five years after surgery to maintain an adequate IOP control (Molteno A C et al., OPHTHALMOLOGY 106(9): 1742-50 (1999)).

For these reasons, surgeons have tried for decades to develop a workable surgery for the trabecular meshwork. The role of uveoescleral drainage, described first in 1965, has become an interesting and new approach to control IOP (A Bill, INVEST OPHTHALMOL 4(5): 911-9 (1965)). Studies have demonstrated a negative hydrostatic pressure from the anterior chamber to the suprachoroidal space (Jordan J F, et al., J GLAUCOMA 15(3): 200-5 (2006)). When the filtration bleb is flat or not obvious and the patient has a good IOP control, the participation of uveoescleral outflow may be larger (Ito K, et al., J GLAUCOMA 11(6): 540-2 (2002)).

Therefore, described herein is a new surgical device and surgical procedure that is faster, safer, and less expensive than currently available modalities.

SUMMARY OF THE DISCLOSURE

In one embodiment, a bent surgical device, comprising an elongate cannula including a cannula wall defining a cannula lumen, a distal beveled end of the cannula including a long side and a short side, a notch through the cannula wall, open to the cannula lumen and disposed proximally adjacent to the distal beveled end, wherein the notch includes a proximal-facing cutting edge and the cannula forms a bend proximal to said notch. An additional embodiment is wherein the cannula lumen extends longitudinally from the distal beveled end to the bend and the device is solid material proximal to the bend. An additional embodiment is wherein the bend is between about 20 and 40 degrees. An additional embodiment is wherein the bend is about 30 degrees. A further embodiment is wherein the distal beveled end of the cannula is closed. A further embodiment is wherein the notch is generally centered in parallel alignment with the long axis of the device at a point about half-way between the long side and the short side. A further embodiment is wherein the notch occupies 240 degrees of the circumference of the cannula wall. A further embodiment is wherein the device is solid steel proximal to the bend. A further embodiment is wherein the device has the dimensions of a 22 gauge needle.

Another embodiment is a method for forming a channel in the eye with a bent surgical device, comprising the steps of contacting the eye with said bent surgical device and cutting a channel in the eye with a notch in said bent surgical device wherein, said bent surgical device comprises an elongate cannula including a cannula wall defining a cannula lumen, a distal beveled end of the cannula including a long side and a short side, a notch through the cannula wall, open to the cannula lumen and disposed proximally adjacent to the distal beveled end, wherein the notch includes a proximal-facing cutting edge and the cannula forms a bend longitudinally aligned with and proximal to said notch, and wherein the cannula lumen extends longitudinally from the bend to the distal beveled end and the device is solid material proximal to the bend. A further embodiment is wherein said notch removes the center flap of a limbus-based scleral flap subdivided into three flaps. A further embodiment is wherein the remaining two flaps are inserted into the suprachoroidal space to form a channel to direct the aqueous humor from the anterior chamber to the suprachoroidal space.

Another embodiment is a method for performing a trabeculectomy with suprachoroidal derivation, comprising the steps of creating a fornix-based conjunctival incision, performing a Tenon's capsule dissection and episcleral vessel cauterization, creating a limbus-based scleral flap of 50% scleral thickness that reaches clear cornea, creating a second limbus-based scleral flap of 30% scleral thickness inside of said limbus-based scleral flap, subdividing the inner limbus-based scleral flap into three flaps by cutting along the anterior-posterior axis, using a bent surgical device to remove the central of said three flaps, performing an incision located posterior to the limbus in the remaining 20% scleral thickness to reach the suprachoroidal space with said surgical device, dissecting the suprachoroidal space, performing a bite in the posterior lip of said scleral incision, inserting the remaining two lateral flaps into the suprachoroidal space to form a channel to direct the aqueous humor from the anterior chamber to the suprachoroidal space, and covering the channel with the first scleral flap in order to create a tunnel and suturing with one stitch in each corner and two stiches in each of the three sides of the flap to obtain a watertight seal, wherein, said bent surgical device comprises an elongate cannula including a cannula wall defining a cannula lumen, a distal beveled end of the cannula including a long side and a short side, a notch through the cannula wall, open to the cannula lumen and disposed proximally adjacent to the distal beveled end, wherein the notch includes a proximal-facing cutting edge and the cannula forms a bend longitudinally aligned with and proximal to said notch, and wherein the cannula lumen extends longitudinally from the bend to the distal beveled end and the device is solid material proximal to the bend.

BRIEF DESCRIPTION OF DRAWINGS

FIG. 3: A side view of the opposite side of the surgical device shown in FIG. 2.
FIG. 4: An angled view of the surgical device.

DETAILED DESCRIPTION OF THE INVENTION

As used herein, the term "proximal" refers to the handle-end of a device held by a user, and the term "distal" refers to the opposite end.

Figure 1:
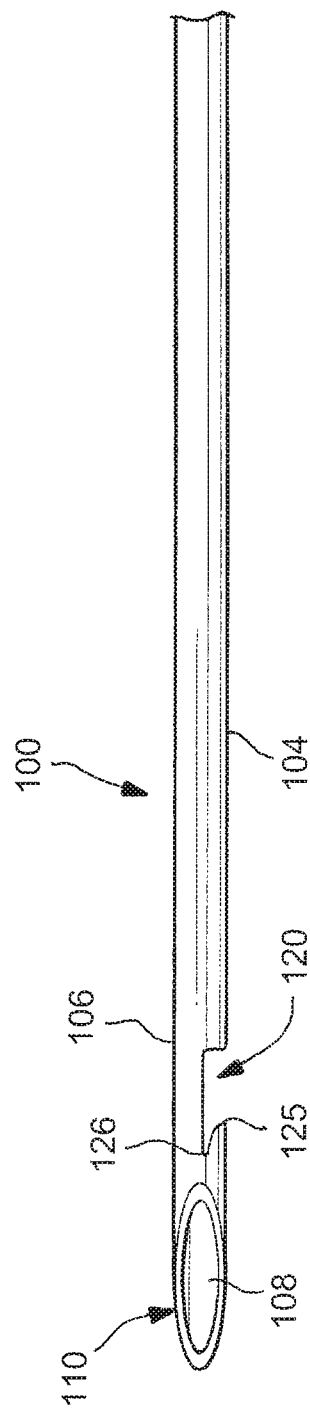
FIG. 1: A top plan view of the surgical device.
Figure 2:
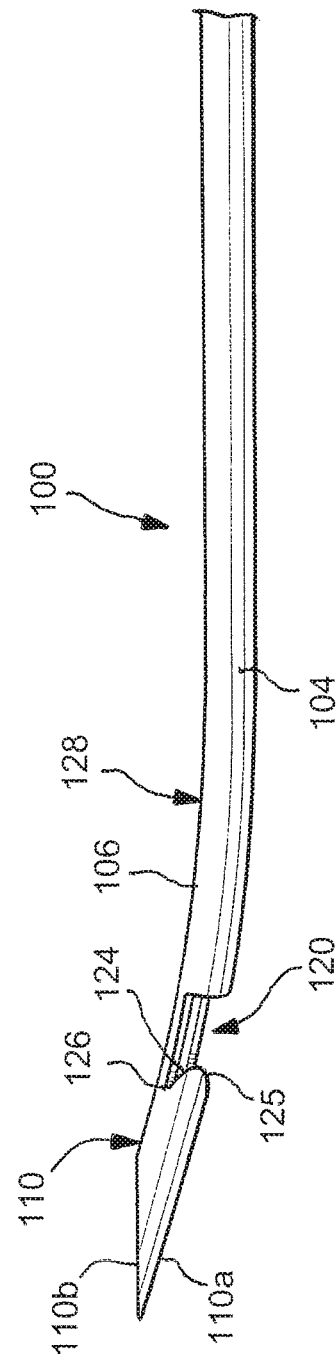
FIG. 2: A side view of the surgical device.
Figure 5:
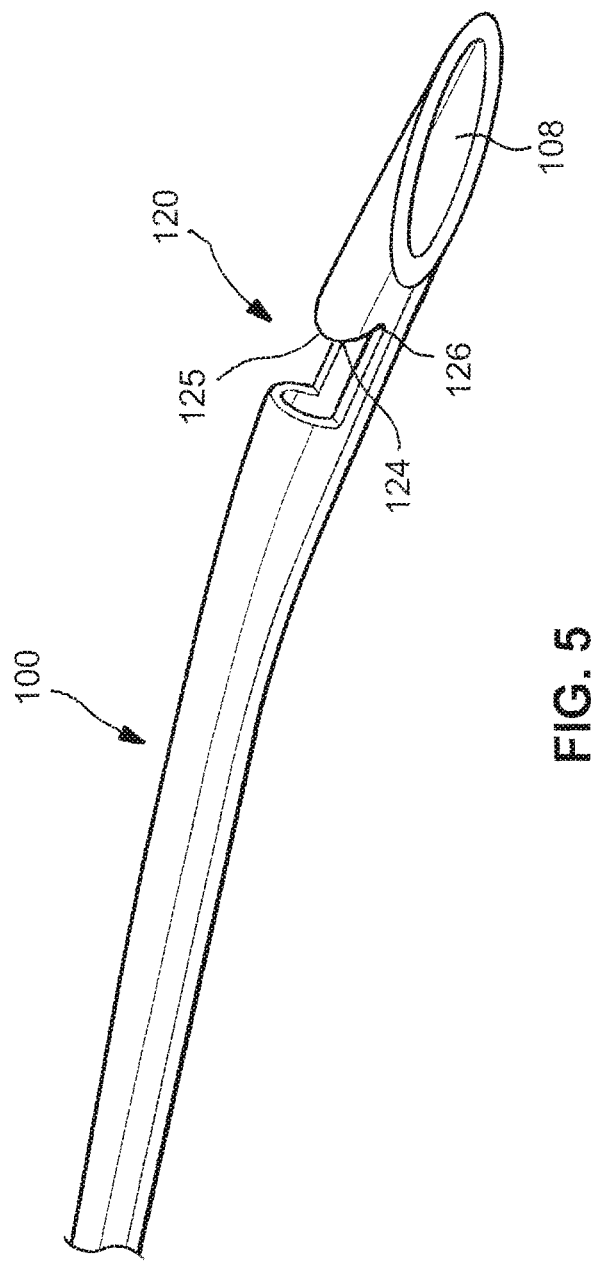
FIG. 5: An alternate angled view of the surgical device from the view shown in FIG. 4.
Figure 6:
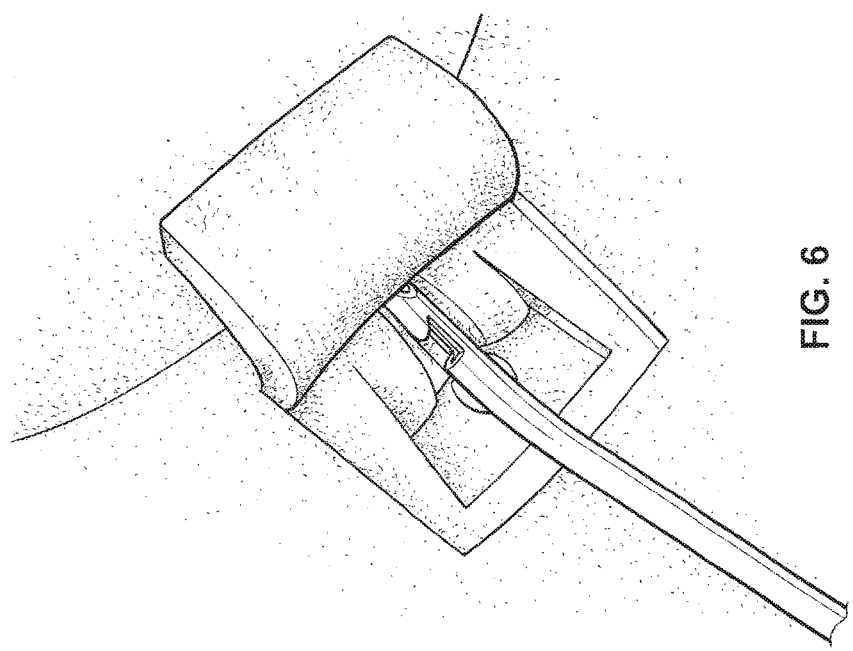
FIG. 6: View of the surgical device inserted into a model of the eye.

One embodiment of the surgical device is described with references to FIGS. 1-5. As shown in the top plan view of FIG. 1, the device 100 includes an elongate cannula 104 at the distal end. The cannula includes a cannula wall 106 that defines a cannula lumen 108. A distal end 110 of the cannula 104 is beveled, including a long side 110a substantially parallel with a section of the central longitudinal axis of the cannula 104 and extending to its distal-most tip end. A short side 110b of the beveled distal end is opposite the long end 110a. As shown in FIGS. 1-5, a notch 120 is disposed proximally adjacent to the distal beveled end 110 and is generally centered in longitudinal alignment at a point about half-way between the long beveled end side 110a and the short beveled end side 110b. In preferred embodiments, the notch 120 is defined on its proximal side by a straight edge intersecting two straight lateral notch sides. The distal edge 124 of the notch 120 preferably is formed as generally parabolic lip that joins the two straight lateral notch sides at a pair of lip end portions 126 that preferably provide a curved transition between the two straight lateral notch sides and the distal edge 124. In one embodiment the lip end portions 126 form an inner bevel of 45°. A central distal lip portion 125 of the distal edge 124 preferably forms a proximal-facing cutting edge. In preferred embodiments, the notch will occupy about two-thirds of the circumference of the cannula 104 at the broadest point of the notch. Proximal to the notch, the cannula forms a bend 128 longitudinally aligned with said notch. This bend can be between about 20 and 40 degrees. In a preferred embodiment, the bend is about 30 degrees. The eye has a curvature and the bend may conform to this curvature, as seen in FIG. 6. In some embodiments the notch length is about 3.5 mm and the length of the distal beveled end is about 6 mm from the bend to the distal beveled end. In other embodiments the distal beveled end has a 30° bevel. The device is solid material proximal to the bend. In other embodiments, the distal beveled end of the cannula 110 is closed, such that the lumen extending longitudinally from the bend or notch to the distal beveled end terminates at the distal beveled end. The device can be made out of any suitable material that has been used to prepare surgical instruments, such as stainless steel, carbon steel, titanium, or alloys of the same. The proximal-facing cutting edge can be an integral part of the device or replaceable and can be made out of any suitable material that has been used to prepare cutting edges, such as diamond, tungsten carbide, or sapphire. In one exemplary embodiment, the device may have the dimensions of a 22 gauge needle made of stainless steel, with an inner diameter of about 0.4 mm (about 0.01 inches).

A method for performing a trabeculectomy with suprachoroidal derivation is described, using the bent surgical device of FIGS. 1-5. In one embodiment of the method, the method comprises the steps of creating a creating a fornix-based conjunctival incision, performing a Tenon's capsule dissection and episcleral vessel cauterization, creating a limbus-based scleral flap of 50% scleral thickness (flap 1) that reaches clear cornea, creating a second limbus-based scleral flap of 30% scleral thickness (flap 2) inside of said limbus-based scleral flap (flap 1), subdividing the inner limbus-based scleral flap (flap 2) into three flaps by cutting along the anterior-posterior axis, and removing the central strip of the subdivided inner limbus-based scleral flap (flap 2), performing an incision located posterior to the limbus in the remaining 20% scleral thickness to reach the suprachoroidal space with the surgical device, dissecting the suprachoroidal space, performing a bite in the posterior lip of said scleral incision, inserting the remaining two lateral flaps into the suprachoroidal space to form a channel about 2½ or 3 millimeters to direct the aqueous humor from the anterior chamber to the suprachoroidal space. A model of the eye following formation of the channel is shown in FIG. 6.

Covering the channel with the first scleral flap in order to create a tunnel and suturing the first flap with one stitch in each corner and two stiches in each of the three sides of the flap to obtain a watertight seal, wherein, said surgical device comprises an elongate cannula including a cannula wall defining a cannula lumen, a distal beveled end of the cannula including a long side and a short side, a notch through the cannula wall, open to the cannula lumen, wherein the notch is disposed proximally adjacent to the distal beveled end and is generally centered in longitudinal alignment at a point half-way between the long beveled end side and the short beveled end side, wherein the notch includes a distal lip defined by a portion of the cannula wall, the distal lip configured to extend proximally from a distal-most end of the notch such that a central distal lip portion is disposed proximal of lip end portions that are continuous with generally longitudinal lateral sides of the notch, wherein the distal lip includes a proximal-facing cutting edge and the cannula forms a bend longitudinally aligned with and proximal to said notch, and wherein the cannula lumen extends longitudinally from the bend to the distal beveled end and the device is solid steel proximal to the bend.

While the present surgical device and surgical procedure has been described with reference to preferred embodiments, these are to be regarded as illustrative rather than limiting. The surgical device and surgical procedure to be protected is defined by the following claims.

What is claimed is:

1. A bent surgical device, comprising:
   an elongate cannula including a cannula wall defining a cannula lumen;
   a distal beveled end of the cannula including a long side and a short side;
   a notch through the cannula wall, open to the cannula lumen and disposed proximally adjacent to the distal beveled end;
   wherein the notch includes a proximal-facing cutting edge and the cannula forms a bend proximal to said notch,
   wherein the notch is generally centered in parallel alignment with the long axis of the device at a point about half-way between the long side and the short side and about half-way between an outer side of the bend and an inner side of the bend, and
   wherein the cannula lumen extends longitudinally starting from the distal beveled end and ending at the bend whereby the device is solid material proximal to the bend.

2. The bent surgical device according to claim 1, wherein the bend is between about 20 and 40 degrees.

3. The bent surgical device according to claim 1, wherein the bend is about 30degrees.

4. The bent surgical device according to claim 1, wherein the distal beveled end of the cannula is closed.

5. The bent surgical device according to claim 1, wherein the notch occupies 240 degrees of the circumference of the cannula wall.

6. The bent surgical device according to claim 1, wherein the device is solid steel proximal to the bend.

7. The bent surgical device according to claim 1, wherein the device has the dimensions of a 22 gauge needle.

* * * * *